United States Patent
Schröer et al.

(10) Patent No.: US 11,477,370 B2
(45) Date of Patent: Oct. 18, 2022

(54) METHOD FOR RECONSTRUCTING AN OUTPUT IMAGE AND/OR A SEQUENCE OF OUTPUT IMAGES FROM RAW IMAGE DATA, IMAGE RECORDING DEVICE, IMAGE RECORDING SYSTEM, AND OVERALL SYSTEM

(71) Applicant: SCHÖLLY FIBEROPTIC GMBH, Denzlingen (DE)

(72) Inventors: Stefan Schröer, Freiburg (DE); Matthias Kühn, Freiburg (DE); Alexander Köhler, Freiburg (DE); Daniel Härter, Emmendingen (DE); Joachim Jauss, Rheinhausen (DE)

(73) Assignee: SCHÖLLY FIBEROPTIC GMBH, Denzlingen (DE)

( * ) Notice: Subject to any disclaimer, the term of this patent is extended or adjusted under 35 U.S.C. 154(b) by 0 days.

(21) Appl. No.: 17/243,631

(22) Filed: Apr. 29, 2021

(65) Prior Publication Data
US 2021/0344835 A1   Nov. 4, 2021

(30) Foreign Application Priority Data

Apr. 30, 2020   (DE) ............... 10 2020 111 776.0

(51) Int. Cl.
*H04N 5/765* (2006.01)
*H04N 5/232* (2006.01)
(Continued)

(52) U.S. Cl.
CPC ..... *H04N 5/23229* (2013.01); *A61B 1/00011* (2013.01); *A61B 1/00045* (2013.01); *G06T 7/0014* (2013.01); *H04N 5/765* (2013.01); *H04N 5/91* (2013.01); *A61B 1/042* (2013.01); *G06T 2207/10068* (2013.01); *G06T 2207/30168* (2013.01); *H04N 2005/2255* (2013.01)

(58) Field of Classification Search
None
See application file for complete search history.

(56) References Cited

U.S. PATENT DOCUMENTS

2007/0081724 A1* 4/2007 Zhang ............... G06V 10/26
                                                382/128
2009/0087020 A1* 4/2009 Yamaguchi ......... G06T 1/0071
                                                382/100

(Continued)

FOREIGN PATENT DOCUMENTS

EP      2423874 A1    2/2012
WO   2015162409 A1  10/2015

*Primary Examiner* — Eileen M Adams
(74) *Attorney, Agent, or Firm* — Grogan, Tuccillo & Vanderleeden, LLP (57) ABSTRACT

The invention relates to a method for reconstructing an output image and/or a sequence of output images from raw image data, wherein, in at least one reconstruction chain between a recording of raw image data by means of an image recording device and a display of the output image and/or the sequence of output images on a display unit, at least one reconstruction step for reconstructing the output image and/or the sequence of output images is carried out, and wherein the result of the at least one reconstruction step is discarded when the result is recognized as invalid with respect to the fulfillment of a verification criterion.

15 Claims, 5 Drawing Sheets

(51) Int. Cl.
*H04N 5/91* (2006.01)
*G06T 7/00* (2017.01)
*A61B 1/00* (2006.01)
*A61B 1/04* (2006.01)
*H04N 5/225* (2006.01)

(56) References Cited

U.S. PATENT DOCUMENTS

| | | | |
|---|---|---|---|
| 2015/0198684 A1* | 7/2015 | Basha | G01R 33/546 |
| | | | 324/309 |
| 2017/0200270 A1 | 7/2017 | Reicher et al. | |
| 2019/0128990 A1* | 5/2019 | Tang | G01R 33/5608 |
| 2019/0285713 A1* | 9/2019 | Polak | G01R 33/5611 |
| 2020/0096588 A1* | 3/2020 | Vester | G01R 33/5611 |

* cited by examiner

METHOD FOR RECONSTRUCTING AN OUTPUT IMAGE AND/OR A SEQUENCE OF OUTPUT IMAGES FROM RAW IMAGE DATA, IMAGE RECORDING DEVICE, IMAGE RECORDING SYSTEM, AND OVERALL SYSTEM

CROSS-REFERENCE TO RELATED APPLICATIONS

This application claims priority to German Patent Application No. 10 2020 111 776.0, filed on Apr. 30, 2020, which is herein incorporated by reference in its entirety.

FIELD OF THE INVENTION

The invention relates to a method for reconstructing an output image and/or a sequence of output images from raw image data, wherein the raw image data is processed in at least two consecutive and/or parallel reconstruction stages and a corresponding sequence of reconstructed output images is output.

The invention further relates to an image recording device, an image recording system, and an overall system.

BACKGROUND OF THE INVENTION

Methods of the kind mentioned at the outset for reconstructing an output image and/or a sequence of output images from raw image data are already known and are used, in particular, in medical technology, for example in order to further process raw images that were recorded by means of an endoscope.

However, especially in medical technology, it is necessary for a user, for example a surgeon, to be shown output images that are correctly reconstructed, i.e. that do not contain any incorrect image information, in particular.

A further problem is that, when an output image is displayed in real time, there must not be too long of a lag time between the recording of a raw image and the display of the output image on a display unit. Lag time plays an important role in endoscopic interventions, in particular, as a delay in the display of output images, for example due to the reconstruction of the output images taking too long, means that the output images can no longer reproduce the real-time situation with sufficient accuracy. In the worst case, this can lead to a surgeon inflicting injury upon a patient, because it is impossible for him or her to discern his or her position within a body cavity from the output images.

The problem is therefore to create a method of the kind mentioned at the outset, by means of which the quality of the output images is improved and/or the usage properties of an image recording device, in particular an endoscope, are improved.

This problem is solved according to claimed embodiments of the invention.

SUMMARY OF THE INVENTION

In particular, according to an embodiment of the invention, in order to solve the aforementioned problem, a method of the kind mentioned at the outset is proposed, which is characterized in that the second reconstruction stage is output as the output image when the second reconstruction stage, compared to the first reconstruction stage, is recognized as valid in a computer-assisted manner and the first reconstruction stage is output as the output image when the second reconstruction stage, compared to the first reconstruction stage, is recognized as invalid in a computer-assisted manner.

In particular, according to an embodiment of the invention, in order to solve the aforementioned problem, a method of the kind mentioned at the outset is proposed, which is characterized in that, for reconstructing the output image and/or the sequence of output images, at least one computing unit of a first computing instance and at least one further computing unit of a higher computing instance are used, which define at least two reconstruction stages, whereby independent computing processes are carried out in different computing steps, wherein a first image of the first reconstruction stage is reconstructed by the first computing unit and a further image of the higher reconstruction stage, building upon the first image, is reconstructed by the at least one further computing unit, [and] that, in a verification step, the at least one image of a higher reconstruction stage is verified with respect to the presence of a verification criterion, wherein, as the output image and/or as part of the sequence of output images, the image having the highest reconstruction stage for which the verification criterion is valid is displayed.

In particular, according to an embodiment of the invention, in order to solve the aforementioned problem, a method of the kind mentioned at the outset is proposed, which is characterized in that in a reconstruction chain between an input of raw image data and an output of the output image and/or the sequence of output images, at least one reconstruction step for reconstructing the output image and/or the sequence of output images is performed, wherein the result of the reconstruction step is discarded when the result is recognized as invalid.

The raw image data can preferably be recorded with an image recording device, in particular an endoscope, wherein an output image and/or a sequence of output images is reconstructed from the raw image data by a computing unit before the output image and/or a sequence of output images is displayed on a display unit.

Advantageous configurations of the invention are described below, which, alone or in combination with the features of other configurations, can optionally be combined with the features of Claim 1 and/or 2 and/or 3.

For example, it can be provided, according to an advantageous development, that the first reconstruction stage and the second reconstruction stage are carried out consecutively or at the same time. In particular, it can thus be achieved that the output image is reconstructed more quickly.

For example, the first reconstruction stage can be established in order to reconstruct a basic output image, wherein the second and/or even further reconstruction stages are established in order to reconstruct additional items of information on the basic output image. The second reconstruction stage and/or the further reconstruction stages can utilize different raw image data than the first reconstruction stage. For example, the second reconstruction stage and/or the further reconstruction stages can utilize raw image data from an infrared image recording device, whereas the first reconstruction stage utilizes raw image data from an image recording device in order to record images in the spectrum that is visible to humans. Alternatively or in addition, the images of a higher reconstruction stage can build upon images of the first reconstruction stage and/or a lower reconstruction stage, i.e. they can refine resulting image content, in particular.

However, according to a further embodiment variant, it can also be provided that the different reconstruction stages utilize the same raw image data. Different reconstructions (in particular for reconstructing different image contents of the at least one output image) or the same reconstructions (in particular for establishing redundancy between the reconstruction stages, preferably of the same computing instance) can be carried out using the at least two reconstruction stages.

In the case of different reconstructions for the at least two reconstruction stages, the image contents can be merged in a merger step in order to display an output image with merged, in particular different, image contents, wherein the image contents originate from at least two reconstruction stages, provided that the validity check was positive, i.e. it has been found in particular that the image contents are compatible with each other.

If the same computing processes are carried out in different reconstruction stages, in particular reconstruction stages located in the same hierarchy, it can be provided that the individual reconstruction stages are carried out redundantly and, after each reconstruction step, it is checked whether at least one of the two redundantly generated computing results (in particular the image content and/or output image) is valid or invalid. For the display of an output image and/or for the further reconstruction of subsequent reconstruction stages, only the valid computing results (i.e., if applicable, intermediate computing results) are then processed further.

The validity check can be directed toward the verification of different selectable parameters, as required. For example, it can be provided that the validity check of the computing result checks for compliance with an upper time limit in order to not exceed a maximum tolerable lag time when displaying an output image after recording raw image data using an image recording device. Lag times of 80 ms or more can be critical, because, for example during surgical operations, there is too much of a delay between the displayed output image and the actual situation.

According to a further development, it can be provided that, in the verification step, a feature comparison is carried out at least between the first and the further image of a higher reconstruction stage, wherein the presence of a specific feature, in particular of the first image, is used as the verification criterion. The first image can preferably be displayed as the output image and/or as part of the sequence of output images when at least one specific feature is not contained in the further image of a higher reconstruction stage, wherein the further image of a higher reconstruction stage is displayed as the output image and/or as part of the sequence of output images when at least one specific feature is contained in the further image. It can thus be ensured that a correctly reconstructed image or image contents are displayed to a user.

According to an advantageous development, it can be provided that a time measurement is carried out in the verification step, wherein the image having the highest reconstruction stage is displayed as the output image and/or as part of the sequence of output images, said image having been reconstructed in good time before the expiry of a maximum, in particular definable and/or predefinable, lag time. Thus, a maximum tolerable lag time can be established in order to be able to ensure that the displayed situation does not deviate too greatly from the recorded situation from a chronological perspective.

According to a further advantageous development, it can be provided that more than two computing units are used, which define a corresponding number of different reconstruction stages and/or at least partially redundant reconstruction stages. In particular, a feature comparison can be carried out in the verification step at least between images of adjacent reconstruction stages and/or between the first image and the image of the respective reconstruction stage. By increasing the reconstruction stages, the number of consecutive and/or simultaneous computing processes can thus be increased. In this way, a desired output image can occasionally be reconstructed more quickly, or it is possible to better ensure that at least one of the computing results is valid due to the carrying out of parallel, redundant computing processes (in particular based upon images of the same reconstruction stage).

According to a further preferred embodiment, the first computing unit can be a local computing unit that is part of the image recording device and/or part of an image recording system, wherein the at least one further computing unit can be an external computing unit. In particular, the further computing unit can be connected to the image recording device and/or to the image recording system via a network infrastructure. It is thus possible for at least a portion of the computing processes to be carried out in a spatially separate manner from the location where the raw image data is recorded, in order to thus reduce the space requirement at the location of the recording and/or to be able to design an image recording device as compact as possible.

According to a further advantageous embodiment, it can be provided alternatively or in addition to the aforementioned embodiments that the at least one further computing unit is designed as a server and/or as a cloud infrastructure that is accessible via the internet and/or as a grid computing infrastructure. For example, the server can be usable by multiple image recording devices and/or image recording systems (i.e. at least connected via a network infrastructure).

According to an advantageous development, it can be provided that different algorithms are processed in the different reconstruction stages, such as algorithms for reconstructing one or two or more additional items of information from super resolution, 3D matching, superimposition of computer tomography data, superimposition of magnetic resonance imaging data, or image correction. Thus, in addition to the typical image content of an output image, additional items of information can be displayed to a user in order to make his or her work easier.

According to a further advantageous embodiment, the first computing unit can process a basic algorithm, which is required in any case in order to reconstruct an output image and/or the sequence of output images. For example, this can be at least one output image in the spectrum that is visible to humans. In particular, at least one specific feature of the first image of the first reconstruction stage can be contained in and/or allocated to all images of the higher reconstruction stage, provided that a correct reconstruction and/or allocation of the images of the higher reconstruction stage to the image of the first reconstruction stage has occurred. This can be verified during the validity check, such that the image or the image content of a higher reconstruction stage is only displayed when the specific feature can be identified and/or allocated.

According to a further advantageous embodiment, at least one feature or a combination of two or more features of the time stamp, image content, and/or specific identifier can be used as the specific feature.

According to a particularly preferred embodiment, it can be provided that an assignment of the computing units forming the computing instances to the reconstruction stages is fixed. This allows the computing processes to be processed particularly quickly in order to be able to display an output image particularly quickly after the raw image data has been recorded.

In particular, according to the invention, in order to solve the aforementioned problem, an image recording device, in particular an endoscope and/or a camera head, is proposed, which is characterized in that the image recording device comprises at least one local computing unit and a connection point for at least one external computing unit and that, for this purpose, the image recording device is established in order to carry out the method as described and/or claimed herein.

As a further solution, an image recording system having at least one image recording device, as described and/or claimed herein, and an external computing unit and/or a display unit is proposed.

In addition, according to the invention, in order to solve the aforementioned problem, an overall system consisting of at least an image recording device as described and/or claimed herein and/or at least an image recording system as described and/or claimed herein and at least an external computing unit arranged in particular peripherally and/or retrievably on demand, which are connected to one another via a network infrastructure, is proposed.

The invention will now be described in further detail on the basis of multiple exemplary embodiments, but is not limited to these exemplary embodiments. Further exemplary embodiments result from the combination of the features of individual or multiple claims with one another and/or with individual or multiple features of the exemplary embodiments.

BRIEF DESCRIPTION OF THE DRAWINGS

FIG. 2 depicts an overview of the method steps of a further possible embodiment variant of the method according to the invention for reconstructing an output image and/or a sequence of output images from raw image data, wherein three consecutive reconstruction stages of different computing instances are provided, wherein, in the implementation of the second and third reconstruction stage, a redundancy is established by means of two computing units of a second computing instance and two computing units of a third computing instance, wherein, as a particularity of this embodiment variant, the intermediate computing results of the two computing units of the second computing instance can be used as a basis for the further reconstruction for each of the two computing units of the third computing instance, such that the reconstruction chains intersect in this embodiment variant, FIG. 3 shows an overview of the method steps of a further possible embodiment variant of the method according to the invention for reconstructing an output image and/or a sequence of output images from raw image data, wherein three consecutive reconstruction stages of different computing instances are provided, wherein, in the implementation of the second and third reconstruction stage, a redundancy is established by means of two computing units of a second computing instance and two computing units of a third computing instance, wherein, as a particularity of this embodiment variant, the intermediate computing results of the two computing units of the second computing instance can each be used only as a basis for the further reconstruction by a computing unit of the third computing instance that is permanently allocated to the respective reconstruction chain, such that the reconstruction chains do not intersect in this embodiment variant, but rather run parallel to each other, FIG. 4 is an overview of the method steps of a further possible embodiment variant of the method according to the invention for reconstructing an output image and/or a sequence of output images from raw image data, wherein three consecutive reconstruction stages of different computing instances are provided, wherein, in the implementation of the first, second, and third reconstruction stage, a redundancy is established by means of two computing units of a first computing instance, two computing units of a second computing instance, and two computing units of a third computing instance, wherein, as a particularity of this embodiment variant, both computing units of the respective computing instance are each permanently allocated to only one reconstruction chain, such that all computing processes between the two completely separated reconstruction chains are redundant and/or run parallel.

DETAILED DESCRIPTION

FIGS. 1-4 show different exemplary embodiments of a method according to the invention for reconstructing an output image 10, 22, 23, 24 and/or a sequence of output images 10, 22, 23, 24 (in the case of a video signal) from raw image data 11 (in particular, input images that have been recorded by an image recording device 1), wherein the raw image data 11 is processed in at least two consecutive and/or parallel reconstruction stages 15, 16, 17, and an output image 10, 22, 23, 24 and/or a corresponding sequence of reconstructed output images 10, 22, 23, 24 is output.

Figure 5:
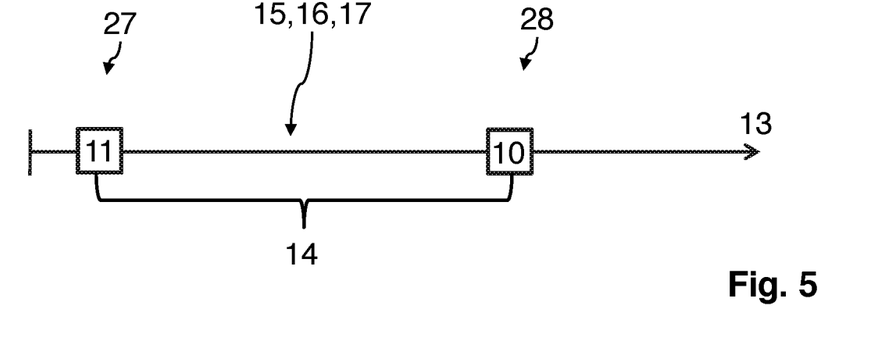
FIG. 5 depicts a timeline from the input of an input image (raw image data) until the output of at least one output image reconstructed in a reconstruction chain, wherein the reconstruction chain comprises at least one computing instance in which at least one reconstruction step is carried out, wherein a total of three reconstruction steps based upon the embodiment variant in FIG. 1, a total of at least five reconstruction steps (possibly seven reconstruction steps) based upon the embodiment variant in FIG. 2, a total of at least five reconstruction steps based upon the embodiment variant in FIG. 3, and a total of at least six reconstruction steps based upon the embodiment variant in FIG. 4, are carried out in order to reconstruct an output image.

FIG. 5 shows a timeline 13 between the input 27 of raw image data 11, e.g. through the recording of a scene, and the output 28 after the image reconstruction. The details of the image reconstruction are described in detail below. The period between input 27 and output 28 is the lag time 14.

Figure 6:
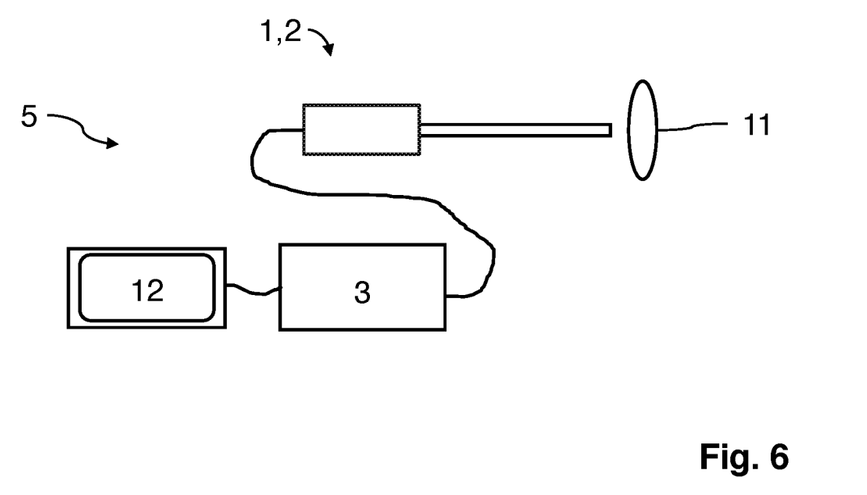
FIG. 6 is a schematic overview of a possible embodiment variant of an image recording device according to the invention and an image recording system according to the invention, which is designed here as an endoscopy system.

FIG. 6 shows a possible embodiment variant of an image recording system 5 with an image recording device 1, which is designed here as an endoscope, in particular as a medical endoscope.

The methods shown in FIGS. 1-4 and described in detail below have the following features in common and therefore pursue a common inventive idea.

Each method processes a reconstruction chain 26, which runs from an input 27 of raw image data 11 until an output 28 of the output image 10, 22, 23, 24 and/or the sequence of output images 10, 22, 23, 24. The reconstruction chain 26 can have one or more reconstruction stages 15, 16, 17 of the images 22, 23, 24, which are reconstructed by at least one computing unit 3, 4, 8, 9 for each computing instance 19, 20, 21. Image contents are reconstructed in each reconstruction stage 15, 16, 17. The image contents between the images 22, 23, 24 of different reconstruction stages 15, 16, 17 can vary and/or increase in complexity as the reconstruction stage 15, 16, 17 increases.

In a verification step (validity check) 18 of the method, a verification criterion is checked in order to determine whether the reconstructed image 22, 23, 24 of the respective reconstruction stage 15, 16, 17 is valid (i.e. whether the verification criterion is fulfilled).

The reconstruction chain 26 thus comprises at least one reconstruction step for reconstructing the output image 10, 22, 23, 24 and/or the sequence of output images 10, 22, 23, 24, wherein the result of the reconstruction step—i.e. the reconstructed images 22, 23, 24—is discarded when the result is recognized as invalid. In this case, the image 22, 23, 24 is displayed as an output image 10, which is recognized as valid.

The methods shown in FIGS. 1-4 are designed in such a way that a second reconstruction stage 16 is output as the output image 10, 23 when the second reconstruction stage 16, compared to a first reconstruction stage 15, is recognized as valid in a computer-assisted manner, and that the first reconstruction stage 15 is output as the output image 10, 22 when the second reconstruction stage 16, compared to the first reconstruction stage 15, is recognized as invalid in a computer-assisted manner.

In addition, in the method shown in FIGS. 1-4, it is provided that, for reconstructing the output image 10, 22, 23, 24 and/or the sequence of output images 10, 22, 23, 24, at least one computing unit 3, 4, 8, 9 of a first computing instance 19 and at least one further computing unit 3, 4, 8, 9 of a higher computing instance 20, 21 are used, which define at least two reconstruction stages 15, 16, 17, whereby independent computing processes are carried out in different computing steps, wherein a first image 22 of the first reconstruction stage 15 is reconstructed by the first computing unit 3 and a further image 23, 24 of the higher reconstruction stage 16, 17, preferably building upon the first image 22, is reconstructed by the at least one further computing unit 4, 8, 9, [and] that, in a verification step 18, the at least one image 23, 24 of a higher reconstruction stage 16, 17 is verified with respect to the presence of a verification criterion 25, wherein, as the output image 10, 22, 23, 24 and/or as part of the sequence of output images 10, 22, 23, 24, the image 22, 23, 24 having the highest reconstruction stage 15, 16, 17 for which the verification criterion 25 is valid is displayed.

Figure 1:
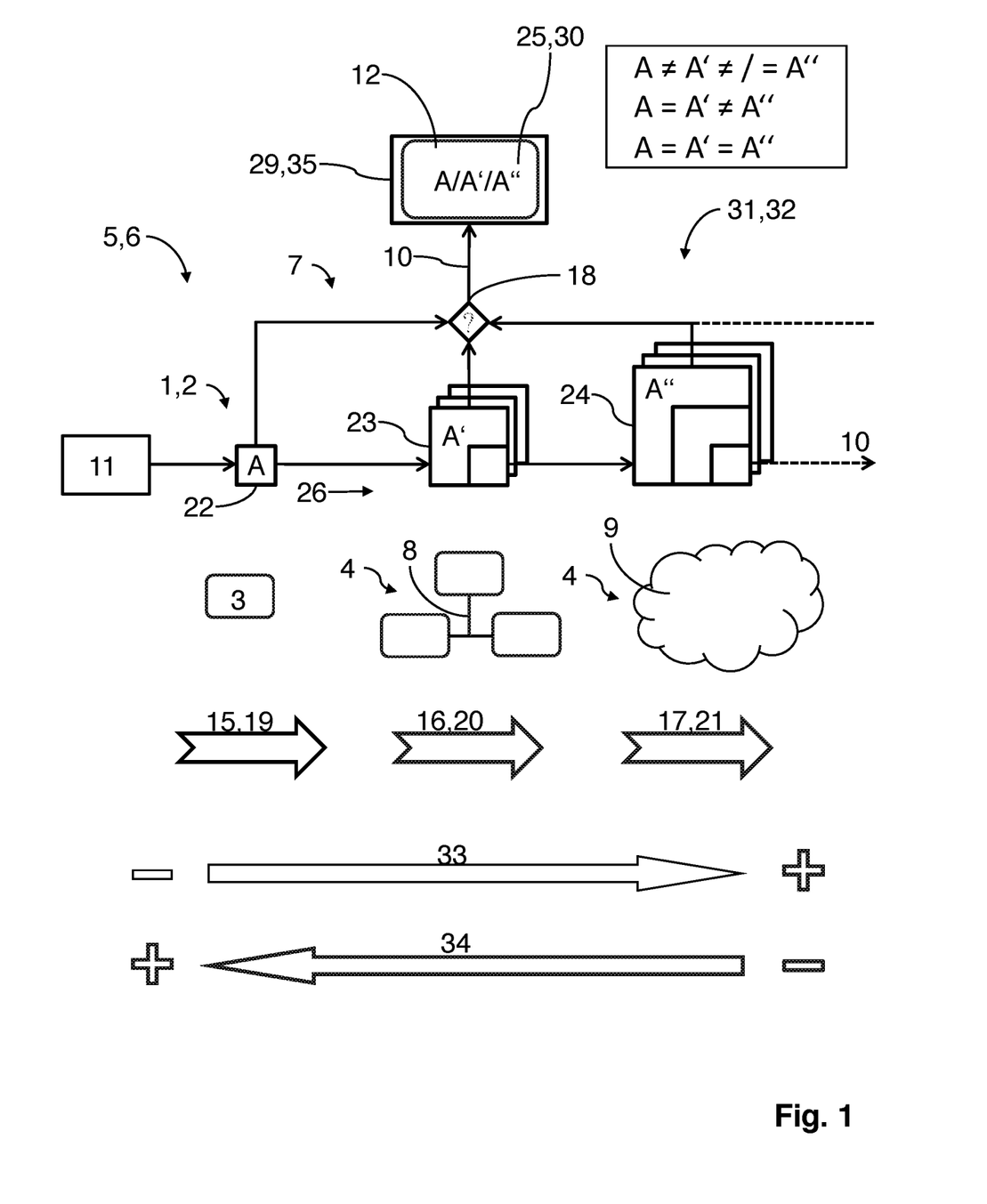
FIG. 1 contains an overview of the method steps of a possible embodiment variant of the method according to the invention for reconstructing an output image and/or a sequence of output images from raw image data, wherein three consecutive reconstruction stages of different computing instances are provided.

FIG. 1 shows a method with a single reconstruction chain 26, wherein each computing instance 19, 20, 21 is formed by a computing unit 3, 4, 8, 9 in order to compute an image 22, 23, 24, which is allocated to the first reconstruction stage 15, the second reconstruction stage 16, and the third reconstruction stage 17, respectively.

Figure 2:
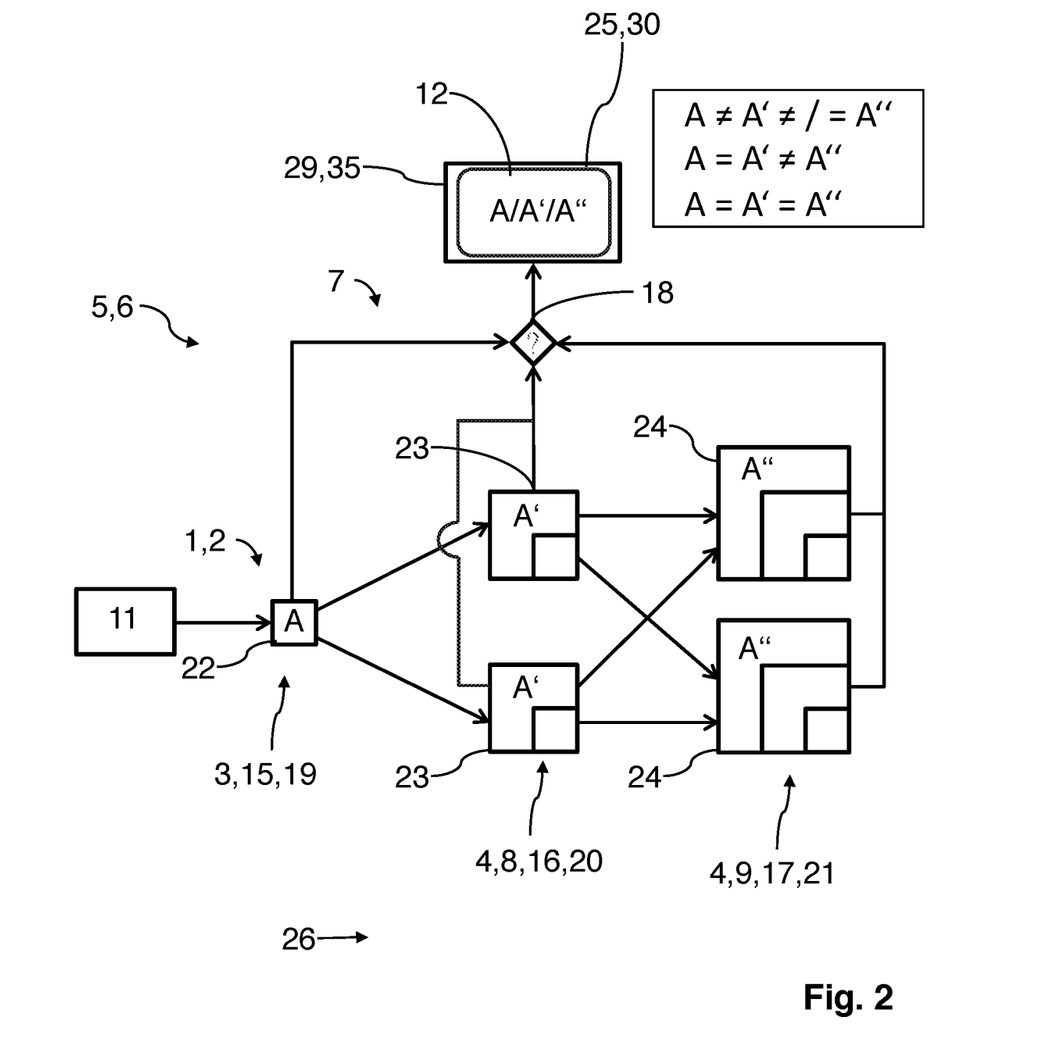

FIG. 2 shows a method with two reconstruction chains 26 that intersect in part, wherein, for reconstructing the second and third reconstruction stages 16, 17 of the images 23, 24, two computing units 3, 4, 8, 9 are implemented per computing instance 20, 21.

Figure 3:
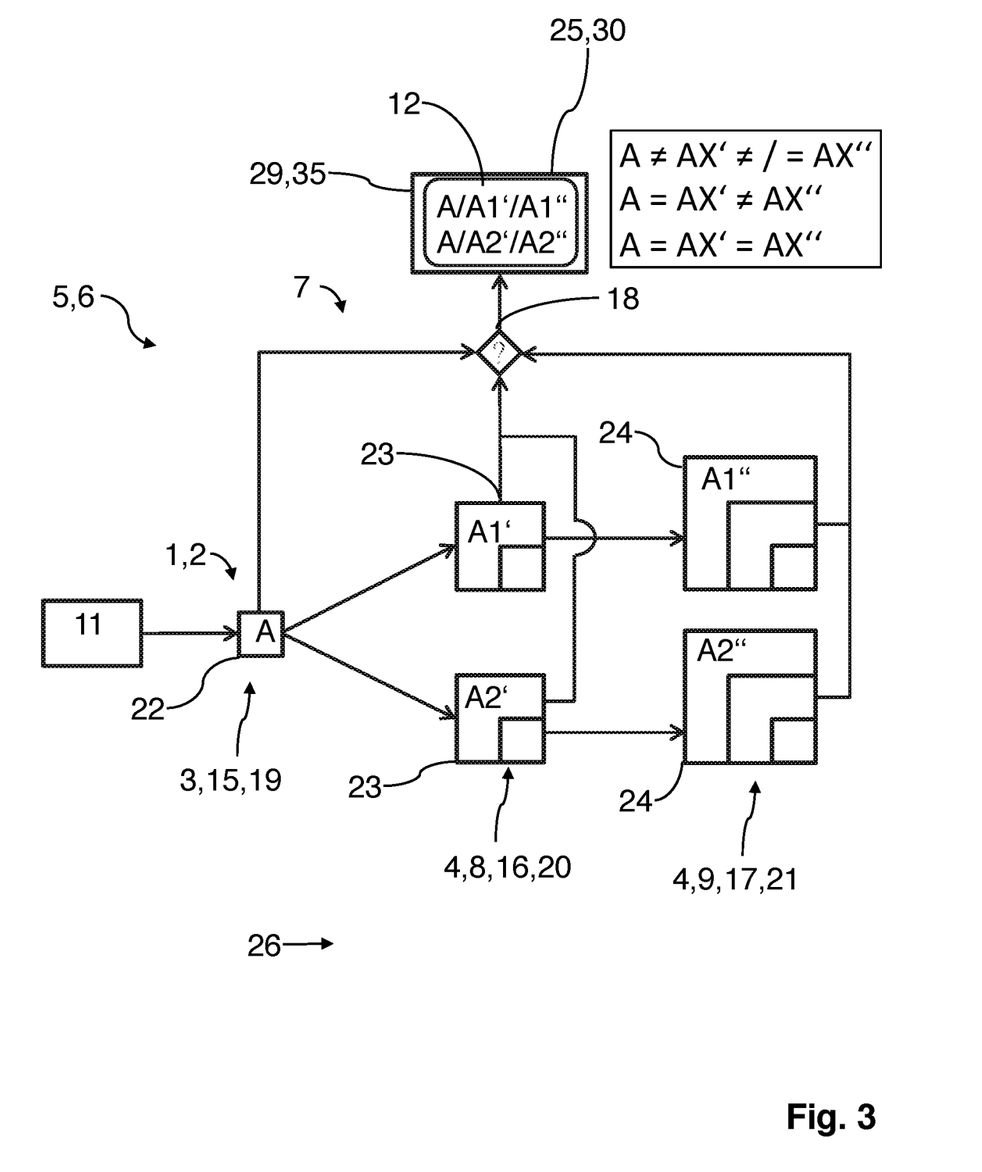
Figure 4:
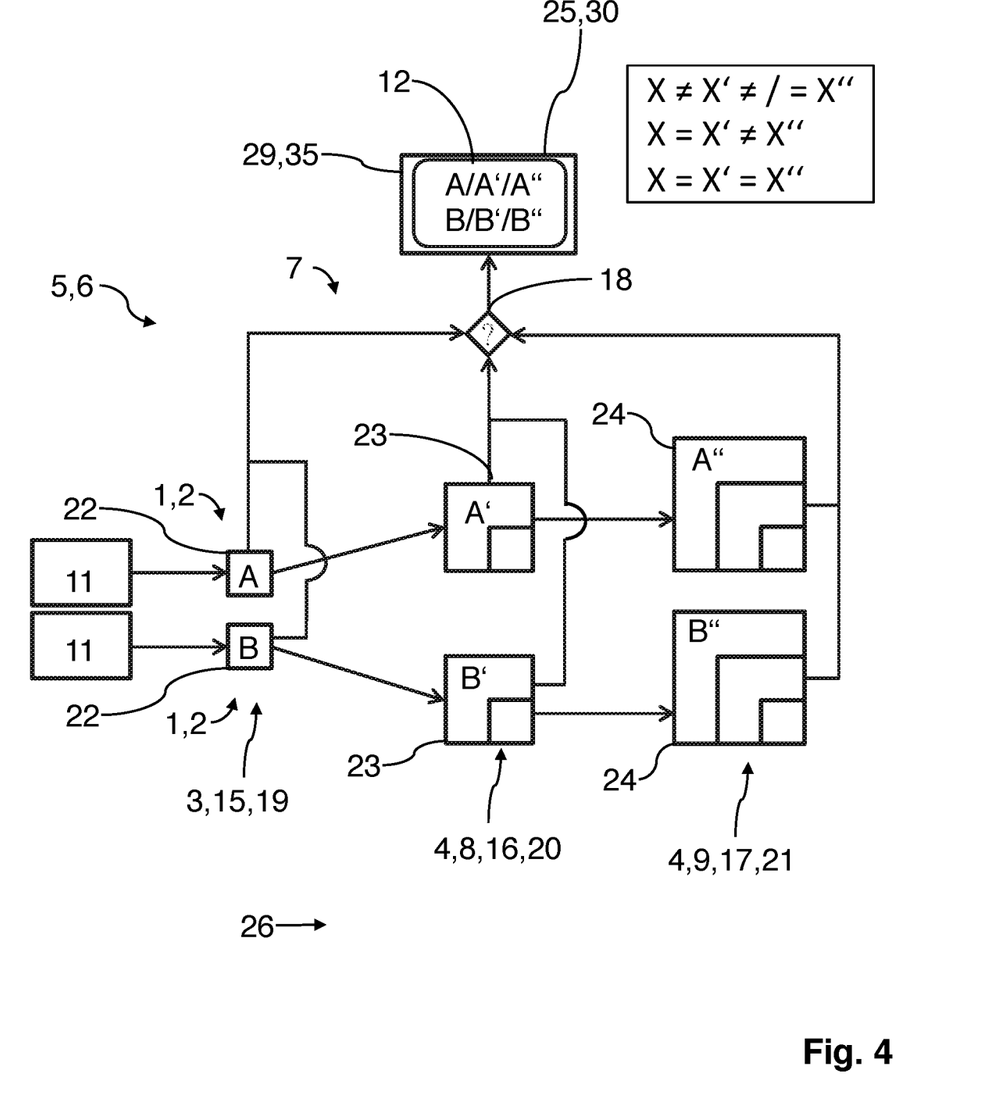

FIGS. 3 and 4 each show methods in which two separate reconstruction chains 26 are processed, wherein, using the method shown in FIG. 3, there is a splitting into the two parallel reconstruction chains 26 after the first reconstruction stage 15, and wherein, using the method shown in FIG. 4, there is a separation of the reconstruction chains 26 from the start, such that two separate computing units 3 are also used in the first computing instance 19 in order to reconstruct images 22 of the first reconstruction stage 15.

In order to check the validity of a reconstructed image 22, 23, 24, a verification step 18 is carried out.

According to a possible embodiment variant, a verification criterion required for the recognition of the validity of an image 22, 23, 24 can relate, for example, to a specific feature 30.

Thus, in the verification step, a feature comparison 29 is carried out at least between the first reconstructed image 22 of the reconstruction chain 26 and the further image 23, 24 of the higher reconstruction stage 16, 17, for example between the image 22 of the first reconstruction stage 15 and the image 23 of the second reconstruction stage 16 and/or between the image 23 of the second reconstruction stage 16 and the image 24 of the third reconstruction stage 17 and/or between the image 22 of the first reconstruction stage 15 and the image 24 of the third reconstruction stage 17. In this case, the presence of the specific feature 30, A, A', A", for example of the first image 22 and/or the second image 23 and/or the third image 24, is used as the verification criterion 25. The first image 22 is displayed as the output image 10 and/or as part of the sequence of output images 10 when at least one specific feature 30, A, A', A" is not contained in the further image 23, 24 of a higher reconstruction stage 16, 17, wherein the further image 23, 24 of higher reconstruction stage 16, 17 is displayed as the output image 10 and/or as part of the sequence of output images 10 when at least one specific feature 30, A, A', A" is contained in the further image 23, 24.

In other words, this means: $A \neq A' \neq /= A''$, i.e. the image 23 of the second reconstruction stage 16 having the feature A' does not contain the feature A, such that either the image 22 having A or the image 24 having A" is displayed as the output image 10 when the feature A is identifiable in the image 24 of the third reconstruction stage 17. However, it can also be provided that the reconstruction chain 26 terminates when a specific feature 30 cannot be identified in the image of the subsequent reconstruction stage 16, 17.

If the image 23 having feature A' comprises the feature A from the image 22, but the image 24 having feature A" does not comprise the feature A and/or A', then the image 23 of the second reconstruction stage 16 is displayed as the output image 10 (therefore, in this case: $A = A' \neq A''$)

If the feature A and/or the feature A' can be identified in the image 24 of the third reconstruction stage 17, then the image 24 is displayed as the output image (therefore, in this case: $A = A' = A'''$). This situation applies to the embodiment variants of FIGS. 1 and 2

It is similar when or more than two parallel reconstruction chains 26 and/or a split into two or more than two separate reconstruction chains 26 is provided, as in the methods shown in FIGS. 3 and 4

In the method shown in FIG. 3, two separate reconstruction chains 26 are processed starting from the second reconstruction stage 16, and thus two feature comparisons 29 are carried out in parallel, such that the following applies here: $A \neq AX' \neq /= AX''$ (image 22 or image 24 are displayed) or $A = AX' \neq AX''$ (image 23 is displayed) or $A = AX' = AX''$ (image 24 is displayed), wherein X stands for 1 or 2.

In the method shown in FIG. 4, two separate and/or non-intersecting reconstruction chains 26 are processed in parallel from input 27 until output 28. Thus, the following applies here: X≠X'≠/=X" (image 22 or image 24 are displayed) or X=X'≠X" (image 23 is displayed) or X=X'=X" (image 24 is displayed), wherein X stands for A or B. It can also be provided that three or more than three separate and/or non-intersecting reconstruction chains 26 are processed in parallel. For example, this can be provided when a multi-chip image recording device comprising multiple image sensors, such as a multi-chip camera head, in particular a three-chip camera head, is used. It is conceivable that a reconstruction chain 26 is provided for each individual image sensor (chip) of the camera head.

Alternatively or in addition, the verification step can relate to a maximum duration for carrying out a reconstruction step in a computing instance 19, 20, 21 by a computing unit 3, 4, 8, 9. A time measurement can thus be carried out in the verification step 18, wherein the image 22, 23, 24 having the highest reconstruction stage 15, 16 is displayed as the output image 10, 22, 23, 24 and/or as part of the sequence of output images 10, 22, 23, 24, 17, said image having been reconstructed in good time before the expiry of a maximum, in particular definable and/or predefinable, lag time 14. If the reconstruction of an image 22, 23, 24, in particular an image 23, 24 of a higher reconstruction stage 16, 17, takes too long, such that the maximum lag time 14 is not observed, then the image of the next lower reconstruction stage 15, 16, 17 is automatically displayed, which possibly contains less image and/or information content than the image 22, 23, 24 of the current reconstruction stage 15, 16, 17 that cannot be completed in time. It can thus be achieved, in particular, that there is a maximum lag of e.g. 80 milliseconds between input 27 (e.g. image recording) and output 28 (e.g. display on the display unit 12). This lag is not yet perceived by the user and does not restrict him or her when performing an endoscopic procedure, in particular.

In each computing instance 19, 20, 21, multiple computing units 3, 4, 8, 9, i.e. in particular Camera Control Units (abbreviated: CCUs), can be provided.

In addition to the three computing instances 19, 20, 21 shown in the exemplary embodiments, the reconstruction chains 26 can comprise further computing instances. Alternatively or in addition, the computing instances 19, 20, 21 can comprise multiple reconstruction stages 15, 16, 17 computed in parallel as the two parallel reconstruction stages 15, 16, 17 shown in the exemplary embodiment. This can be achieved, for example, by further computing units 3, 4, 8, 9 per computing instance 19, 20, 21 or by parallel computing processes carried out by one computing unit 3, 4, 8, 9.

In the variant embodiments of the method shown in FIGS. 1-4, the first computing unit 3 is designed as a local computing unit, which can be, for example, part of the image recording device 1 by means of which a scene is recorded, i.e. by means of which raw image data 11 is generated.

In the method shown in FIG. 4, the images 22, A, B of the first reconstruction stage 15 can be reconstructed by two different computing units 3 or by one computing unit 3, or two or more than two separate image recording devices 1 can even be provided for the respective recording of the scene, such that already different raw image data 11 is used as input images.

The computing units 3, 4, 8, 9 of the second and higher computing instances 20, 21 can similarly be local computing units 3 or, as shown in FIGS. 1-4, external computing units. For example, external computing units can refer to local cloud computing units 8 or external cloud computing units 9, which are connected to the image recording device 1 via a network infrastructure 7. The use of external computing units offers the advantage that the space required on site, for example in an operating room, can be kept relatively low, however, it is still possible for more complex computing processes to be carried out externally and for the reconstruction result to be displayed locally, for example in the operating room.

In particular, it can be provided that at least one external computing unit 4, 8, 9 takes the form of a server, in particular a server that can be used by multiple image recording devices 1 and/or image recording systems 5, and/or takes the form of a cloud infrastructure 31 that is accessible via the internet and/or as a grid computing infrastructure 32.

It can be particularly advantageous when different algorithms are processed in the different reconstruction stages 15, 16, 17, such as algorithms for reconstructing one or two or more additional items of information from super resolution, 3D matching, superimposition of computer tomography data, superimposition of magnetic resonance imaging data, or image correction, in particular.

The first computing unit 3 can preferably process a basic algorithm that is required in any case in order to reconstruct an output image 10, 22, 23, 24 and/or the sequence of output images 10, 22, 23, 24 (in particular because the reconstruction stages build upon each other). The at least one specific feature 30 of the first image 22 of the first reconstruction stage 15 is thus contained in and/or can be allocated to all images 23, 24 of the higher reconstruction stage 16, 17, provided that a correct reconstruction and/or allocation of the images 23, 24 of the higher reconstruction stage 16, 17 to the image 22 of the first reconstruction stage 15 has occurred.

As explained above, the specific feature 30 can be determined relatively freely depending on the field of application. When used with an endoscope 2, one or a combination of two or more of the features of the group consisting of the time stamp, image content, and/or specific identifier can be considered as the specific feature 30.

As shown in the individual FIGS. 1-4, using the reconstruction chains 26, it is advantageous when the computing units 3, 4, 8, 9 forming the computing instances 19, 20, 21 are permanently allocated to the reconstruction stages 15, 16, 17. In other words, this means that a fixed allocation is established in the order of the computing units 3, 4, 8, 9 for each reconstruction chain 26, wherein said allocation preferably cannot be influenced by any user. The reconstruction chains 26 can preferably be one-dimensional in form, such that a kind of fixed series connection of the computing units 3, 4, 8, 9 is established.

The images 22, 23, 24 of different reconstruction stages 15, 16, 17 can be combined with one another, in particular in a merger step (assembly step) 35 before and/or after the validity check 18 in order to form an output image 10, such that the different image contents of the images 22, 23, 24 can be displayed in one output image 10. Only the image content of the images 22, 23, 24 that has been checked as valid is recorded and displayed.

The invention therefore relates in particular to a method for reconstructing an output image 10, 22, 23, 24 and/or a sequence of output images 10, 22, 23, 24 from raw image data (11), wherein, in at least one reconstruction chain 26 between a recording of raw image data 11 by means of an image recording device 1 and a display of the output image 10, 22, 23, 24 and/or the sequence of output images 10, 22, 23, 24 on a display unit 12, at least one reconstruction step for reconstructing the output image 10, 22, 23, 24 and/or the sequence of output images 10, 22, 23, 24 is carried out, and wherein the result of the at least one reconstruction step is discarded when the result is recognized as invalid with respect to the fulfillment of a verification criterion 25.

What is claimed is:

1. A method for reconstructing an output image and/or a sequence of output images from raw image data comprising:
    processing raw image data in at least two consecutive and/or parallel reconstruction chains each chain including at least a first reconstruction stage and a second reconstruction stage;
    performing a verification step on the output of the highest reconstruction stage of a reconstruction chain;
    outputting the second reconstruction stage of a reconstruction chain as an output image when the second reconstruction stage of the reconstruction chain, compared to the first reconstruction stage of the reconstruction chain, is recognized as valid in a computer-assisted manner; and
    outputting the first reconstruction stage of a reconstruction chain as an output image when the second reconstruction stage of the reconstruction chain, compared to the first reconstruction stage, is recognized as invalid in a computer-assisted manner.

2. A method according to claim 1 wherein the raw image data is recorded with an image recording device, in particular an endoscope, wherein an output image is reconstructed by computing units from the raw image data before the output image is displayed on a display unit; and wherein for the reconstruction of the output image, a first computing unit of a first computing instance and a second computing unit of a second computing instance are used, which define the at least two reconstruction stages whereby independent computing processes are carried out in different computing steps; and wherein an image of the first reconstruction stage is reconstructed by the first computing unit and an image of the second reconstruction stage, building upon the image of the first reconstruction stage, is reconstructed by the second computing unit, and that, in the verification step, the image of the second reconstruction stage is verified with respect to the presence of a verification criterion, wherein, as the output image, the image having the highest reconstruction stage for which the verification criterion is valid is displayed.

3. The method according to claim 1 further comprising:
    discarding the result of the reconstruction when the result is recognized as invalid.

4. The method according to claim 1 wherein the image from the first reconstruction stage is an output image when at least one specific feature is not contained in an image from the second reconstruction stage, and wherein the image from the second reconstruction stage is the output image and/or as part of the sequence of output images when at least one specific feature is contained in the image from the second reconstruction stage.

5. A method according to claim 1 wherein in the verification step, a time measurement is carried out, wherein the image having the highest reconstruction stage is the output image, said image having been reconstructed before the expiry of a definable or pre-definable lag time.

6. A method according to claim 2, wherein more than two computing units are used, which define a corresponding number of different reconstruction stages or at least partially redundant reconstruction; and
    wherein, in the verification step, a feature comparison is carried out between images of the first and second reconstruction stages.

7. A method according to claim 2 wherein the first computing unit is a local computing unit, which is part of the image recording device, and the second computing unit is an external computing unit, which is connected in particular to the image recording device and/or the image recording system via a network infrastructure.

8. A method according to claim 2 wherein the second computing unit is a server that can be used by multiple image recording devices and/or image recording systems, a cloud-based infrastructure that is accessible via the internet, and/or a grid computing infrastructure.

9. A method according to claim 1 wherein in the different reconstruction stages, different algorithms are processed, such as, algorithms for reconstructing one or two or more additional items of information, preferably at least one additional item of information from super resolution, 3D Matching, superimposition of computer tomography data, superimposition of magnetic resonance tomography data, or image correction.

10. A method according to claim 2, wherein the first computing unit processes a basic algorithm, which is required to reconstruct an output image; and
    wherein at least one specific feature of the image of the first reconstruction stage is contained in or can be allocated to all images of the second reconstruction stage, or a higher reconstruction stage, provided that a correct reconstruction and/or allocation of the images of the second or higher reconstruction stage to the image of the first reconstruction stage has occurred.

11. A method according to claim 4 wherein the specific feature is at least one of a time stamp, image content, and/or specific identifier.

12. A method according to claim 2, characterized in that an assignment of the computing units forming the computing instances to the reconstruction stages is fixed.

13. An image recording device, in particular an endoscope and/or camera head comprising:
    at least one local computing unit and a connection point for at least one external computing unit; and
    wherein that the image recording device is set up in order to carry out the method of claim 1.

14. The image recording device of claim 13 further comprising:
    an external computing unit and/or a display unit.

15. The image recording device of claim 14 wherein the image recording device and external computing unit and/or display unit are arranged peripherally and/or retrievably on demand and are connected to one another via a network infrastructure.

* * * * *